United States Patent
Harvey et al.

(10) Patent No.: US 11,919,847 B1
(45) Date of Patent: Mar. 5, 2024

(54) METHOD FOR PRODUCING HIGH-PERFORMANCE AVIATION FUEL BLENDSTOCKS FROM MONOTERPENES

(71) Applicant: The United States of America, as represented by the Secretary of the Navy, Arlington, VA (US)

(72) Inventors: Benjamin G. Harvey, Ridgecrest, CA (US); Karan R. Doppalapudi, Poway, CA (US); Calvin Luke Keller, Ridgecrest, CA (US)

(73) Assignee: United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 18/166,594

(22) Filed: Feb. 9, 2023

Related U.S. Application Data

(60) Provisional application No. 63/394,039, filed on Aug. 1, 2022.

(51) Int. Cl.
    *C07C 5/13* (2006.01)
    *C07C 1/20* (2006.01)
    *C10L 1/06* (2006.01)

(52) U.S. Cl.
    CPC .............. *C07C 5/13* (2013.01); *C07C 1/20* (2013.01); *C10L 1/06* (2013.01); *C07C 2531/025* (2013.01); *C10L 2200/0484* (2013.01); *C10L 2270/04* (2013.01)

(58) Field of Classification Search
    None
    See application file for complete search history.

(56) References Cited

U.S. PATENT DOCUMENTS

| | | | |
|---|---|---|---|
| 9,682,897 B1* | 6/2017 | Harvey | C07C 1/24 |
| 2006/0057058 A1* | 3/2006 | Dahl | C01B 3/382 |
| | | | 423/648.1 |
| 2014/0316177 A1* | 10/2014 | Ge | C07C 1/20 |
| | | | 502/79 |
| 2018/0162789 A1* | 6/2018 | Liu | C07C 31/125 |

OTHER PUBLICATIONS

Yang et al. "Highly efficient conversion of terpenoid biomass to jet-fuel range cycloalkanes in a biphasic tandem process" Green Chemistry, 2017, 19, 3566-3573 (Year: 2017).*

(Continued)

*Primary Examiner* — Youngsul Jeong
*Assistant Examiner* — Alyssa L Cepluch
(74) *Attorney, Agent, or Firm* — Naval Air Warfare Center Weapons Division; Edu Enin-Okut

(57) ABSTRACT

The invention relates to an efficient, high-throughput method of converting monoterpenes to high performance aviation fuel blendstocks. The method is a one pot, two-step process that includes a dehydration step followed by a hydrogenation step. Both steps can proceed without the use of solvents. Use of biosynthetically generated monoterpenes by this method produces sustainable aviation fuel blendstocks having applications that include use as a full-performance or an ultra-performance jet fuel blendstock.

18 Claims, 5 Drawing Sheets

(56) References Cited

OTHER PUBLICATIONS

Li et al. "Rapid Ether and Alcohol C—O Bond Hydrogenolysis Catalyzed by Tandem High-Valent Metal Triflate + Supported Pd Catalysts" and Supporting Information J. Am. Chem. Soc. 2014, 136, 104-107 and S1-S22 (Year: 2014).*

Keskiväli et al. "Transition metal triflate catalyzed conversion of alcohols, ethers and esters to olefins" RSC Advances, 2018, 8 15111-15118 (Year: 2018).*

"Terpene" Hawley's Condensed Chemical Dictionary. 2007 (Year: 2007).*

* cited by examiner

US 11,919,847 B1

METHOD FOR PRODUCING HIGH-PERFORMANCE AVIATION FUEL BLENDSTOCKS FROM MONOTERPENES

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF INVENTION

The invention generally relates to a method of making high density aviation fuels, and more particularly, to a method of converting monoterpenes to cycloalkanes with increased densities and enhanced seal swelling properties useful as sustainable, high density aviation fuel blendstocks.

BACKGROUND

While ground transportation has employed a variety of alternative energy sources to reduce greenhouse gas emissions, the aviation industry has been much more challenging to decarbonize due to the extensive power requirements of aircraft. Despite the challenges, the aviation industry has embraced sustainable aviation fuels (SAFs) that can be used as drop-in replacements for conventional petroleum-based fuels, and in turn, greatly reduce net greenhouse gas emissions.

The demanding requirements of an aviation fuel like a full-performance jet fuel includes a high density (greater than 0.775 g/mL), good low-temperature viscosity (less than 8.0 $mm^2/s$), and a high gravimetric net heat of combustion (greater than 42.8 MJ/kg). Although SAFs can be designed to have a number of properties that exceed those of conventional petroleum-based fuels, renewable aviation fuels have not yet been broadly implemented due to high initial costs and limited supplies. Conventional SAFs based on acyclic alkanes have outstanding gravimetric net heats of combustion, but their low densities and relatively high viscosities, particularly at −40° C., greatly reduce their viability as drop-in replacements.

SUMMARY

To address this challenge, the inventors focused their efforts on the synthesis of SAFs based on cyclic hydrocarbons, in particular, biosynthetically generated terpenes. The method described herein is a one-pot, two-step process that converts biosynthetically generated monoterpenes to cycloalkanes useful as fuel blendstocks, where none of the steps of the method require use of a solvent. These cycloalkanes exhibit high gravimetric heats of combustion, densities greater than 0.8 g/mL, enhanced seal swelling properties, and low kinematic viscosities. Thus, the method provides an efficient, high-throughput fuel production process capable of generating full-performance and ultra-performance biosynthetic aviation fuel blendstocks.

DEFINITIONS

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Reference throughout the specification to "one example", "another example", "an example", and so forth, means that a particular element (e.g., feature, structure, and/or characteristic) described in connection with the example is included in at least one example described below, and may or may not be present in other examples. In addition, it is to be understood that the described elements for any example may be combined in any suitable manner in the various examples unless the context clearly dictates otherwise.

In describing and claiming the examples described below, the singular forms "a", "an", and "the" include plural referents unless the context clearly dictates otherwise.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Example of such limitations include preparing the sample in wet versus a dry environment, different instruments, variations in sample height, and differing requirements in signal-to-noise ratios. The use of numerical values in the various ranges specified in this application, unless expressly indicated otherwise, are stated as approximations as though the minimum and maximum values within the stated ranges are both preceded by the word "about" or "approximately". In this manner, slight variations above and below the stated ranges can be used to achieve substantially the same results as values within the ranges. Also, unless indicated otherwise, the disclosure of these ranges is intended as a continuous range including every value between the minimum and maximum values.

The definitions and understandings of fuels and fuel blendstocks are known to those of skill in the art, and such definitions are incorporated herein for the purposes of understanding the general nature of the subject matter of the present application. However, the following discussion is useful as a further understanding of some of these terms.

DETAILED DESCRIPTION

Exploration of the direct dehydration and cyclization of monoterpenes such as linalool has been conducted in an effort to produce more diverse SAF mixtures with lower viscosities and higher gravimetric heats of combustion. However, known approaches have a number of drawbacks, such as low activity for complete dehydration, the generation of many oxygenated intermediates, and processes that require the use of one or more solvents.

The method described herein is a high-throughput process that converts monoterpenes to fuel blendstocks useful in aviation fuel blends that avoids many of the drawbacks of known processes including those noted above. The high-throughput nature of the method is contributed to by the use of one pot, i.e. one reaction vessel, to conduct its two-step process, where the steps can be solvent-free.

Figure 1:
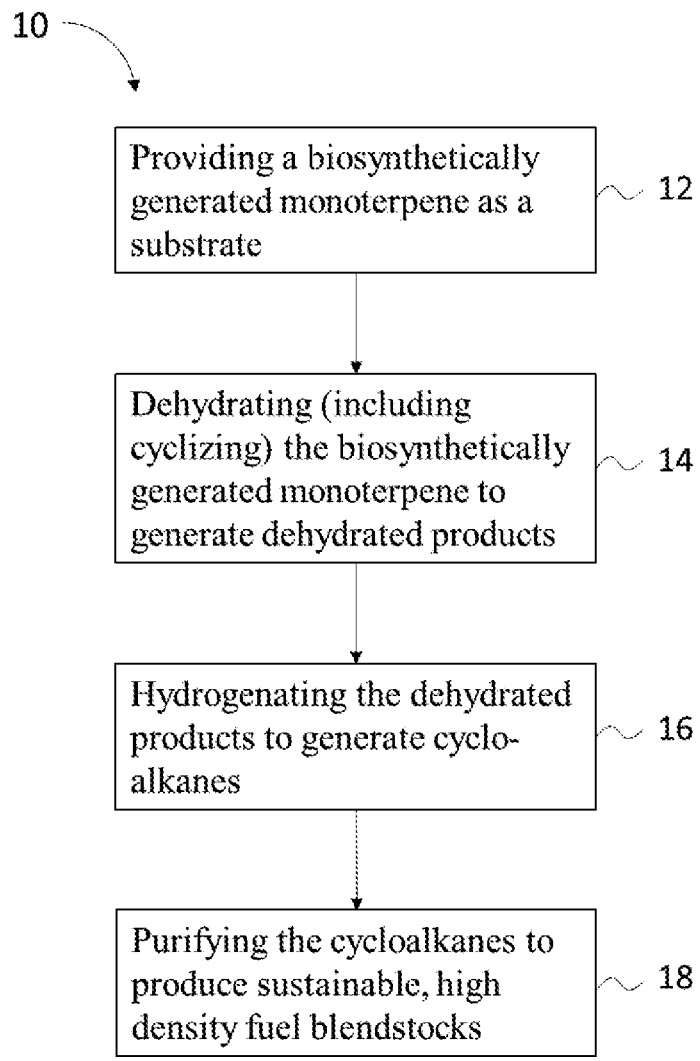
FIG. 1 is a flow diagram depicting an example of the method for converting monoterpenes to cycloalkanes useful as fuel blendstocks.

An example of the method is illustrated in FIG. 1. The method 10 to convert monoterpenes into fuel blendstocks begins at step 12 by providing a monoterpene as a substrate. The monoterpene may be an acyclic monoterpene, a cyclic monoterpene, or a mixture of the two. Preferably, the monoterpene is obtained as a plant extract or synthesized from biological sources. Examples of biosynthetically generated acyclic monoterpenes suitable for use in the method include monoterpene alcohols such as linalool, nerol, geraniol, and myrcenol. Examples of suitable biosynthetically generated cyclic monoterpenes include monoterpene ethers such as 1,8-cineole and 1,4-cineole. Among these, linalool, 1,8-cineole, and 1,4-cineole are preferred.

Next, at step 14 in FIG. 1, the monoterpene serving as a substrate, i.e. a monoterpene alcohol, a monoterpene ether or a mixture of the two, is dehydrated to generate a mixture of products. At step 16, the products are hydrogenated in the same reaction vessel used for the dehydration conducted at step 14. Then, the dehydrated and hydrogenated products, which include cycloalkanes, are purified to produce sustainable, high-density fuel blendstocks at step 18.

Dehydration of the substrate occurs in the presence of an acid catalyst. The dehydration reaction can include cyclization of the monoterpene. A monoterpene alcohol can be cyclized into a cyclic alkene or cyclic oxygenated species. A monoterpene ether can be cyclized into cyclic alkene.

The acid catalyst can be a heterogeneous solid acid catalyst with moderate acidity (a Hammett acidity function $(H_o)$ value of 5 to −5). Examples of the heterogeneous solid acid catalyst include a macroreticular cation exchange resin, acid zeolites, and acid clays. Preferably, the catalyst is a macroreticular cation exchange resin such as an Amberlyst-15. To avoid the formation of oligomeric species, the dehydration reaction can be conducted at a low temperature, such as a temperature ranging from about 0° C. to 100° C. for about 1 hour to 6 hours. Preferably, the reaction is conducted at a temperature below 50° C. Additionally, the dehydration reaction can be conducted with or without a solvent. Conducting the reaction without a solvent is preferred to reduce the number of processing steps in the method.

Hydrogenation of the products of dehydration can occur using a heterogeneous catalyst at a reaction temperature of about 25° C. to about 150° C. The heterogeneous catalyst can be based on a transition metal such as platinum, palladium, nickel, cobalt, and iron. Preferably, the heterogeneous catalyst is platinum-based or nickel-based. If a platinum-based or nickel-based heterogeneous catalyst is used at moderate reaction temperatures (e.g., at about 25° C.), the formation of aromatic compounds such as 1-methyl-4-isopropanylbenzene (p-cymene) can be practically eliminated. An example of a suitable platinum-based, heterogeneous catalyst for hydrogenation is a 10% Pd/C catalyst.

The dehydration step and the hydrogenation step of the method can be conducted in separate reaction vessels. However, it is preferable to conduct both of these steps in the same reaction vessel using a dual catalyst system. Examples of the dual catalyst system include discrete catalysts mixed together (e.g., a mixture of the dehydration catalyst and the hydrogenation catalyst discussed above), and a composite material that contains active sites for both dehydration and hydrogenation. The active sites for dehydration in the composite material will be acidic (e.g., Brønsted or Lewis acids) while the active sites for hydrogenation will contain metals (e.g., Pt, Pd, Ni, Fe, and Co) in low oxidation states. In addition, because the catalysts are heterogeneous, they can be removed by simple filtration and reused.

The dual catalyst system is combined with the substrate. The substrate is heated to preferably about 50° C. in the presence of an inert gas, or under vacuum, to initiate the dehydration reaction. Once the dehydration step is complete, the reactor is placed under a hydrogen atmosphere and the temperature is controlled to promote the formation of hydrogenated products. Purification of the dehydrated and hydrogenated products can be accomplished by distillation.

The amount of aromatic compounds in the resulting fuel blendstock, for example p-cymene as discussed above, can be minimized by controlling the temperature, allowing for complete hydrogenation of the product mixture before further heating is employed, and keeping the hydrogen pressure constant in the reactor. Alternatively, if desired, the hydrogenation reaction can be tuned to produce higher quantities of p-cymene by increasing the reaction temperature or reducing the hydrogen pressure in the reactor. For example, conducting the hydrogenation at 150° C., without initial steps at lower temperatures, can result in the production of a fuel blendstock that includes up to 40 wt. % of p-cymene. Aromatic compounds like p-cymene may be desired due to their efficiency at swelling nitrile rubber elastomers and the role they can play in maintaining engine integrity (as well as preventing fires in flight due to fuel leakage).

Figure 2:
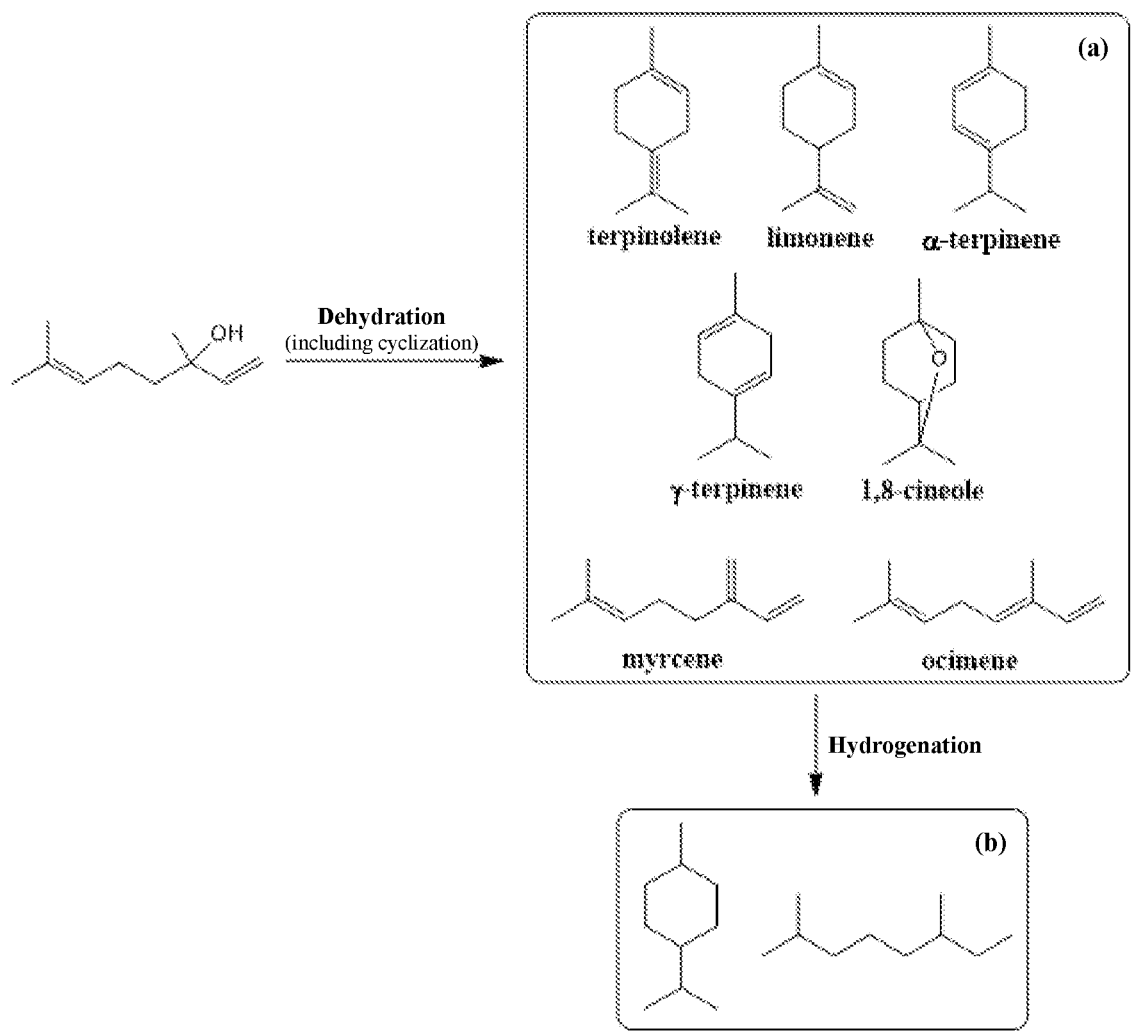
FIG. 2 is a schematic of an example of the method for converting monoterpenes to cycloalkanes using linalool, including a depiction of: (a) the major products generated by the dehydration of linalool using a catalyst, and (b) the major products generated by the hydrogenation of the products shown in (a).
Figure 3:
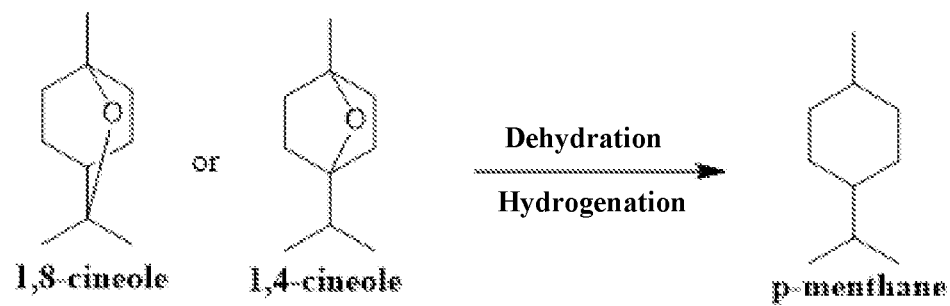
FIG. 3 is a schematic of an example of the method for converting monoterpenes to cycloalkanes using 1,8-cineole or 1,4-cineole as substrates, including a depiction of the major product generated by the dehydration and subsequent hydrogenation of 1,8-cineole or 1,4-cineole.

The method described above allows for the dehydration and hydrogenation of monoterpenes in an efficient one-pot, two-step process. The results of the method are saturated fuel blendstocks which exhibit outstanding gravimetric heats of combustion and low temperature fluidity. The fuel blendstocks include cycloalkanes, such as 1-methyl-4-isopropylcyclohexane (p-menthane) and acyclic alkanes such as 2,6-dimethyloctane (2,6-DMO). As shown in FIG. 2, when the monoterpene used as the substrate in the method is linalool, the fuel blendstock produced is a mixture that contains p-menthane and 2,6-DMO. Small amounts of p-cymene (e.g., about 5% by weight or less) may be produced as well. When 1,8-cineole or 1,4-cineole are used as substrates in the method as shown in FIG. 3, the fuel blendstock produced is almost exclusively p-menthane.

The fuel blendstocks produced using the method described above can be blended with conventional aviation fuels, SAFs, and synthetic paraffinic kerosenes (SPKs). As shown in the table below, a fuel blendstock generated from linalool composed of a mixture that includes p-menthane and 2,6-DMO, also known as isomerized hydrogenated linalool (IHL), has outstanding fuel properties including a higher gravimetric heat of combustion, lower viscosity, and acceptable density, compared to a conventional jet fuel such as Jet-A. These properties suggest that IHL has applications as a blending agent to enhance the properties of conventional jet fuels or existing SAFs such as HEFA-Jet. In addition, other fuel blendstocks made from linalool, such as dimethyltetrahydrodicyclopentadiene isomers (RJ-4) and hydrogenated isobutylene trimers (HIBT), can also be included in fuel blends with 2,6-DMO and/or p-menthane to provide additional flexibility when optimizing the resulting fuel blend to maximize the gravimetric heat of combustion while maintaining acceptable density, seal-swelling capabilities, and other key operability requirements.

| Fuel | Gravimetric NHOC (MJ/kg) | Volumetric NHOC (MJ/L) | Density (g/mL, 15° C.) | Viscosity (mm²/s, −20° C.) | Viscosity (mm²/s, −40° C.) | Hydrogen Content (%) |
|---|---|---|---|---|---|---|
| IHL* | 43.54 | 34.10 | 0.783 | 2.74 | 4.74 | 14.8 |
| p-menthane | 43.20 | 34.72 | 0.804 | 2.98 | 5.19 | 14.4 |
| 2,6-DMO | 43.98 | 32.26 | 0.733 | 2.27 | 3.83 | 15.4 |
| RJ-4 | 42.21 | 39.03 | 0.925 | 18.31 | 49.86 | 12.4 |
| HEFA-Jet | 43.73 | 33.32 | 0.762 | 5.65 | 12.77 | — |
| Jet-A | >42.80 | >33.17 | >0.775 | <8.0 | <12.0 | >13.5 |

(*Data for IHL produced using two-pot method.)

EXAMPLES

The following examples are given as particular embodiments of the invention and to demonstrate the practice and advantages thereof. It is to be understood that the examples are given by way of illustration and are not intended to limit the specification or the claims that follow in any manner.

Methods of Characterization

NMR Spectroscopy.

$^1$H NMR spectra were recorded on a Bruker Avance III 500 spectrometer at 25° C., operating at 400.46 MHz. Proton-decoupled $^{13}$C{$^1$H} NMR spectra were recorded with the same instrument at 25° C., operating at 100.86 MHz. Chemical shifts are reported in parts per million (ppm) downfield from tetramethylsilane, and are referenced relative to the NMR solvent (CDCl$_3$), according to the literature values—$\delta(^1H)$=7.26, $\delta(^{13}C)$=77.16.

Product Distribution Analysis.

Gas chromatography with flame ionization detection (GC-FID) was conducted with an Agilent Technologies 7820A GC system equipped with a DB-5 60 m×0.32 mm×0.25 μm column. GC-FID was conducted using volumes of 10, 15 or 20 mL of isoprene and 17.15 mL of myrcene. After 18 hours, one μL (±0.2 μL) of each sample solution was manually injected into the gas chromatograph, with an inlet split ratio of 25:1, and inlet and detector temperatures of 250° C. and 300° C., respectively. The column temperature was held at 40° C. for 3 minutes, followed by a temperature ramp of 10° C. min$^{-1}$ to 300° C. The fuel compositions were further analyzed with a Thermo Scientific TRACE™ 1310 gas chromatograph-mass spectrometer (GC-MS) (equipped with an Orbitrap™ mass spectrometer), utilizing a TG-5SilMS 30 mm×0.25 mm×0.25 m GC column. The instrument was set to an injection volume of 1 μL, held at 40° C. for 3 minutes, and then ramped at 20° C. min$^{-1}$ to 300° C.

Kinematic Viscosity and Density Studies.

The kinematic viscosities and densities of the fuels and fuel blendstocks were measured using a Stabinger Viscometer, SVM™ 3001, connected to a TC-502 chiller to achieve temperatures down to −40° C. Each sample was placed in a 5 mL syringe which was then attached to the viscometer through a Luer Lock adapter. Approximately 3 mL of each fuel was then slowly injected to pre-wet the measurement cells. The sample was allowed to equilibrate at the starting temperature (typically 20° C.). The method was then initiated and an additional 1 mL of sample was added. Each sample was then cooled to −40° C. (±0.002° C.), and at 5° C. increments, both the kinematic viscosity and density were measured. Reported values were derived from the average of five determinations. After each run, the measuring cells were rinsed three times with hexanes and dried under a stream of nitrogen.

Heat of Combustion (HOC) Determination.

In a typical experiment, a pellet of high-purity benzoic acid (~950-1000 mg) was accurately weighed, and about 350-800 mg of fuel and fuel blendstocks were added and allowed to fully saturate the pellet. The pellet was then re-weighed, and the gross HOC was measured in a Parr 6200 Calorimeter. After combustion of the sample, the gross HOC was corrected by subtracting the contribution due to benzoic acid and combusted wire. The net HOC (NHOC) was then calculated from the corrected gross HOC by taking into account the hydrogen content (determined by elemental analysis (EA)) and the density of the fuels and fuel blendstocks at 15° C. The NHOC measurements were taken in triplicate and averaged.

Preparation of Fuel Blendstocks

Comparative Example. Two-Pot Conversion of Linalool to p-Menthane and 2,6-DMO

Dehydration.

43.70 g of Amberlyst-15 H-Form was added to 432.5 g (500 mL, 2.804 mol) of linalool in a round-bottomed flask. The flask was subsequently transferred to an oil bath at a temperature of 50° C. The mixture was rigorously stirred for 1 hour, and then the catalyst was removed by filtration. The resulting product was composed of a mixture of α-terpinol, terpinolene, γ-terpinene, β-ocimene, limonene, α-terpinene, and myrcene, along with traces of dimers (e.g., terpene dimers and oxygenated terpene dimers). (An example of some of these products is depicted in (a) of FIG. 2.) Then, the monomeric mixture was isolated by fractional vacuum distillation.

Hydrogenation.

21.14 g (25 mL) of the distilled, dehydrated product was transferred to a Parr reactor. 2.41 g of Amberlyst-15 H-Form was added along with 0.21 g of 10% Pd/C. The reactor was evacuated and refilled with hydrogen three times. Finally, the reactor was pressurized to 500 pounds per square inch (psi). The reactor was maintained at or below room temperature (about 25° C.) to prevent formation of p-cymene and allowed to react overnight (about 16 hours). Subsequently, after the uptake of hydrogen ceased, the reactor was gradually heated to 50° C. and maintained at that temperature for three hours while keeping the pressure at 500 psi. The temperature was then raised to 100° C. for 1 hour, followed by a final hour at 150° C. The reactor was then allowed to cool to room temperature and its contents were filtered through a CELITE® pad. The reactor was rinsed with diethyl ether and the resulting slurry was filtered through the CELITE®. The filtrate was transferred to a separatory funnel and washed with a 10% sodium bicarbonate solution, distilled water, and brine. The organic layer was dried with $MgSO_4$, filtered, and the diethyl ether was removed under reduced pressure. Vacuum distillation (at about 2 mmHg) yielded a product mixture of 60 wt. % of p-menthane, 35 wt. % of 2,6-DMO, and 5 wt. % of p-cymene, as confirmed by GC-FID.

Properties of the products and a mixture thereof were determined (i.e. gravimetric NHOC, volumetric NHOC, density, viscosity, and hydrogen content). The properties are presented in the table above.

Figure 4:
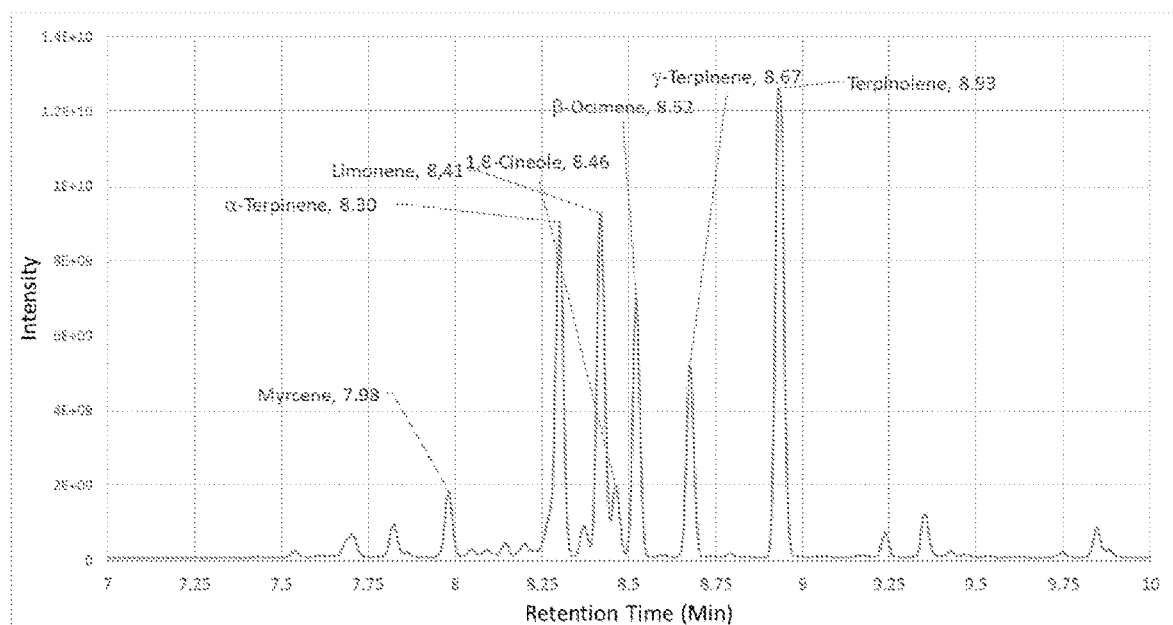
FIG. 4 is a graph of a gas chromatogram of the major products generated by the dehydration of linalool shown in (a) of the schematic depicted in FIG. 2.
Figure 5:
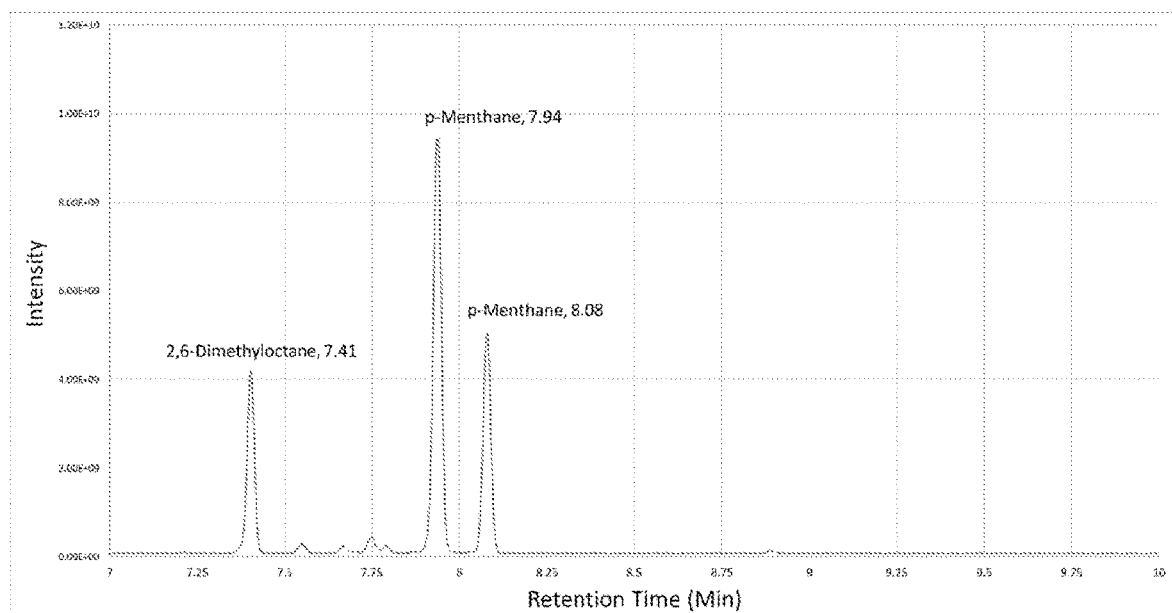
FIG. 5 is a gas chromatogram of the major products generated by the hydrogenation of linalool as shown in (b) of the schematic depicted in FIG. 2.

Example 1. One-Pot Conversion of Linalool to p-Menthane and 2,6-DMO 42.85 g (50 mL, 0.278 mol) of linalool, 4.99 g of Amberlyst-15 H-Form, and 0.48 g of 10% Pd/C were added to a Parr reactor. The reactor was evacuated and heated to 50° C. for 80 minutes with rapid stirring. Then, the temperature of the reactor was lowered to 25° C., and the system was evacuated, purged with hydrogen three times, and pressurized to 500 psi. Rapid stirring was resumed and the temperature was maintained at 20° C. to 25° C. by active cooling of the reactor. The reaction proceeded at room temperature overnight (about 16 hours). Then, while holding the pressure steady at 500 psi, the temperature was gradually raised to 50° C. and maintained at that temperature for an additional 3 hours. The temperature was then raised to 100° C. for one hour, raised to 150° C. for an additional hour, and then cooled to room temperature. The reaction mixture was purified as described in the Comparative Example to yield a product that contained, based on its total weight, 55 wt. % of p-menthane, 41 wt. % of 2,6-DMO, and 3 wt. % of p-cymene, as confirmed by GC-FID. FIG. 4 is a gas chromatogram of the products generated from dehydration of linalool. FIG. 5 is a gas chromatogram of the fuel blendstock generated from hydrogenation of the dehydrated products of linalool.

Example 2. One-Pot Conversion of 1,8-Cineole to p-Menthane 23.31 g (25 mL, 0.151 mol) of 1,8-cineole, 2.38 g of Amberlyst-15 H-Form, and 0.26 g of 10% Pd/C were added to a Parr reactor. The reactor was evacuated, refilled three times with hydrogen, and pressurized to 500 psi. The reactor was heated to 50° C. and stirred until hydrogen uptake ceased, i.e. about 5 hours. Hydrogen was added intermittently to maintain a pressure of 500 psi. The reactor was then warmed to 100° C. and stirred overnight (about 16 hours). On completion, the reaction was allowed to cool to room temperature. The reaction mixture was purified as in Comparative Example to yield a product that contained, based on its total weight, over 95 wt. % of p-menthane. $^1$H NMR spectroscopy showed that the product was composed substantially of p-menthane.

Example 3. One-Pot Conversion of 1,4-Cineole to p-Menthane 20.67 g (22.97 mL, 0.149 mol) of 1,4-cineole, 2.28 g of Amberlyst-15 H-Form, and 0.27 g of 10% Pd/C were added to a Parr reactor. The reactor was evacuated, refilled three times with hydrogen, and pressurized to 500 psi. The reactor was heated to 50° C. and maintained at that temperature for 6 hours. The temperature was then raised to 100° C. for 5 hours. Hydrogen was added intermittently to maintain a pressure of 500 psi. Then, the reactor was cooled to ambient temperature. The reaction mixture was purified as described in the Comparative Example to yield a product that contained, based on its total weight, about 100 wt. % of p-menthane. $^1$H NMR spectroscopy showed that the product was composed entirely of p-menthane.

What is claimed is:

1. A method of converting monoterpenes to cycloalkanes useful as high performance aviation fuel blendstocks, the method comprising:
    providing an oxygenated acyclic monoterpene as a substrate;
    dehydrating the substrate to generate a dehydrated product in a reaction vessel;
    hydrogenating the dehydrated product in the reaction vessel to generate cycloalkanes; and
    purifying the cycloalkanes, thereby producing a fuel blendstock, wherein
        the oxygenated acyclic monoterpene is obtained from one or more plant extracts or is synthesized from biological sources,
        dehydrating the substrate comprises creating a vacuum in the reaction vessel or filling the reaction vessel with an inert gas, and heating the reaction vessel to a temperature of about 0° C. to less than about 50° C. for about 1 hour to about 6 hours,
        hydrogenating the dehydrated products comprises creating a hydrogen atmosphere by pressurizing the reaction vessel using hydrogen to a pressure of about 500 pounds per square inch, and performing a hydrogenation reaction at one or more temperatures from about 25° C. to about 150° C. for about 1 hour to about 15 hours, and
        dehydrating the substrate and hydrogenating the dehydrated product are performed without the use of a solvent.

2. The method of claim 1, wherein the oxygenated acyclic monoterpene is an acyclic monoterpene alcohol comprising linalool.

3. The method of claim 1, wherein dehydrating the substrate and hydrogenating the dehydrated product are performed using a dual catalyst system,
    where the duel catalyst system is either a combination comprising an acid catalyst and a hydrogenation catalyst or a composite material comprising active sites for dehydration and active sites for hydrogenation.

4. The method of claim 3, wherein the acid catalyst comprises at least one of a macroreticular cation exchange resin, an acid zeolite, or an acid clay.

5. The method of claim 4, wherein the acid catalyst is a macroreticular cation exchange resin comprising Amberlyst-15.

6. The method of claim 3, wherein the hydrogenation catalyst is based on a transition metal comprising at least one of platinum, palladium, nickel, cobalt, or iron.

7. The method of claim 3, wherein the active sites for dehydration are acidic and the active sites for hydrogenation contain one or more transition metals.

8. The method of claim 7, wherein the active sites for dehydration comprise at least one of a Brønsted acid or a Lewis acid.

9. The method of claim 7, wherein the active sites for hydrogenation comprise at least one of platinum, palladium, nickel, iron, or cobalt.

10. A method of converting monoterpenes to cycloalkanes useful as high performance aviation fuel blendstocks, the method comprising:
   placing an oxygenated cyclic monoterpene as a substrate in a reaction vessel;
   pressurizing the reaction vessel using hydrogen to a pressure of about 500 pounds per square inch;
   dehydrating the substrate to generate a dehydrated product in the pressurized reaction vessel;
   hydrogenating the dehydrated product in the pressurized reaction vessel to generate cycloalkanes; and
   purifying the cycloalkanes, thereby producing a fuel blendstock, wherein
      the oxygenated cyclic monoterpene is obtained from one or more plant extracts or is synthesized from biological sources,
      dehydrating the substrate comprises heating the reaction vessel to a temperature of about 0° C. to less than about 50° C. for about 1 hour to about 6 hours,
      hydrogenating the dehydrated products comprises a hydrogenation reaction performed at one or more temperatures from about 25° C. to about 150° C. for about 1 hour to about 15 hours, and
      dehydrating the substrate and hydrogenating the dehydrated product are performed without the use of a solvent.

11. The method of claim 10, wherein the cyclic monoterpene is a cyclic monoterpene ether comprising 1,8-cineole, or 1,4-cineole, or a combination thereof.

12. The method of claim 10, wherein dehydrating the substrate and hydrogenating the dehydrated product are performed using a dual catalyst system,
   where the duel catalyst system is either a combination comprising an acid catalyst and a hydrogenation catalyst or a composite material comprising active sites for dehydration and active sites for hydrogenation.

13. The method of claim 12, wherein the acid catalyst comprises at least one of a macroreticular cation exchange resin, an acid zeolite, or an acid clay.

14. The method of claim 13, wherein the acid catalyst is a macroreticular cation exchange resin comprising Amberlyst-15.

15. The method of claim 12, wherein the hydrogenation catalyst is based on a transition metal comprising at least one of platinum, palladium, nickel, cobalt, or iron.

16. The method of claim 12, wherein the active sites for dehydration are acidic and the active sites for hydrogenation contain one or more transition metals.

17. The method of claim 16, wherein the active sites for dehydration comprise at least one of a Brønsted acid or a Lewis acid.

18. The method of claim 16, wherein the active sites for hydrogenation comprise at least one of platinum, palladium, nickel, iron, or cobalt.

* * * * *